United States Patent [19]

Lieberman et al.

[11] 4,012,966

[45] Mar. 22, 1977

[54] KNOB AND CONTROL SHAFT ASSEMBLY WITH BRAKE

[75] Inventors: Lester Lieberman, Kings Point; Ralph Oddo, Dix Hills, both of N.Y.

[73] Assignee: Jan Hardware Manufacturing, Inc., New York, N.Y.

[22] Filed: Nov. 17, 1975

[21] Appl. No.: 632,465

[52] U.S. Cl. .................................. 74/553; 74/531; 64/29; 192/12 R

[51] Int. Cl.$^2$ .................... A61B 5/12; F16D 67/02

[58] Field of Search .................... 74/531, 553, 554; 192/12 R, 8 R, 95; 188/166; 64/29

[56] References Cited

UNITED STATES PATENTS

| | | | |
|---|---|---|---|
| 1,446,652 | 2/1923 | Morris | 74/553 |
| 2,288,955 | 7/1942 | Richardson et al. | 64/29 |
| 2,341,647 | 2/1944 | Parkhurst | 74/553 X |
| 2,600,674 | 6/1952 | Natkins | 64/29 |
| 2,704,466 | 3/1955 | Way | 74/553 X |
| 2,919,602 | 1/1960 | Sparagen | 74/553 |
| 3,198,923 | 8/1965 | Trip | 74/553 |
| 3,561,287 | 2/1971 | Lawrence | 74/553 |

*Primary Examiner*—Benjamin W. Wyche
*Attorney, Agent, or Firm*—J. B. Felshin

[57] ABSTRACT

The knob comprises a body which cannot turn the control shaft unless the body is first pushed in. A brake prevents turning of the knob body when the body is in normal condition. Upon pushing the body rearwardly, the brake is disengaged to allow turning of the knob. Upon releasing the body, spring means projects the body forwardly back to normal condition in which the brake prevents the body from turning. Spring pressed balls allow the body to turn without turning the control shaft upon exerting excessive torque on the body to thereby prevent damage to the controls. Means is provided to limit turning of the control shaft to a predetermined angle.

36 Claims, 6 Drawing Figures

KNOB AND CONTROL SHAFT ASSEMBLY WITH BRAKE

This invention relates to knob and control shaft assemblies.

An object of this invention is to provide a knob of the character described which wholly contains the mechanism which connects the knob body to the control shaft for turning the shaft.

Another object of this invention is to provide a device of the character described in which the knob body must be pushed in before allowing the body to turn the shaft.

Yet another object of this invention is to provide a device of the character described in which spring pressed balls allow the knob body to turn without turning the shaft if the turning torque of the body is excessive, to prevent damage to controls activated by the shaft.

Still another object of this invention is to provide a device of the character described comprising means to limit the angle of rotation of the shaft.

A further object of this invention is to provide in a device of the character described, an insert ring within the knob body fixed to the control shaft, with the body slidable on the ring but rotatable therewith, and a brake within the body having means to lock to the ring, the construction being such that when the body is pushed in, the brake is disengaged from the ring to allow the body and ring to be rotated to turn the control shaft.

A still further object of this invention is to provide in a device of the character described, spring means to slidably move the body outwardly after it has been pushed in, turned and released, and means controlled by outward movement of the body to slidably move the brake into locking engagement with the ring, to prevent turning of the knob body in its retracted, outwardly moved position.

Yet a further object of this invention is to provide a device of the character described in which the brake and ring have part circular groove and pin engageable in the groove to limit angle of rotation of the control shaft.

A still further object of this invention is to provide a device of the character described in which the ring has a plurality of equiangular spaced longitudinal blind bores receiving springs pressing against balls to push them into openings in the knob body, so that if the turning torque on the knob body exceeds a predetermined amount, the knob body can be rotated without turning the control shaft, to thereby prevent damage.

Another object of this invention is to provide a strong, durable, compact and safe knob and control shaft assembly which is easy to manipulate, inexpensive to manufacture, and which shall yet be practical and efficient to a high degree in use.

Other objects of this invention will in part be obvious and in part hereinafter pointed out.

The invention accordingly consists in the features of construction, combinations of elements, and arrangement of parts which will be exemplified in the construction hereinafter described and of which the scope of invention will be indicated in the following claims.

Figure 1:
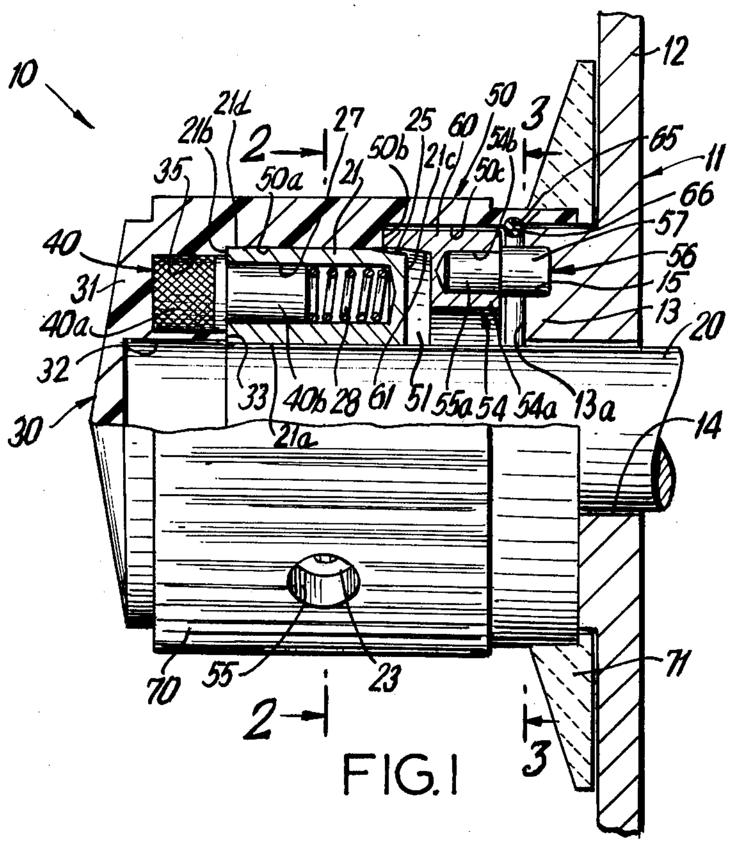
FIG. 1 is a side elevational view with parts broken away and in cross section of a knob and control shaft assembly embodying the invention mounted on a panel.
Figure 2:
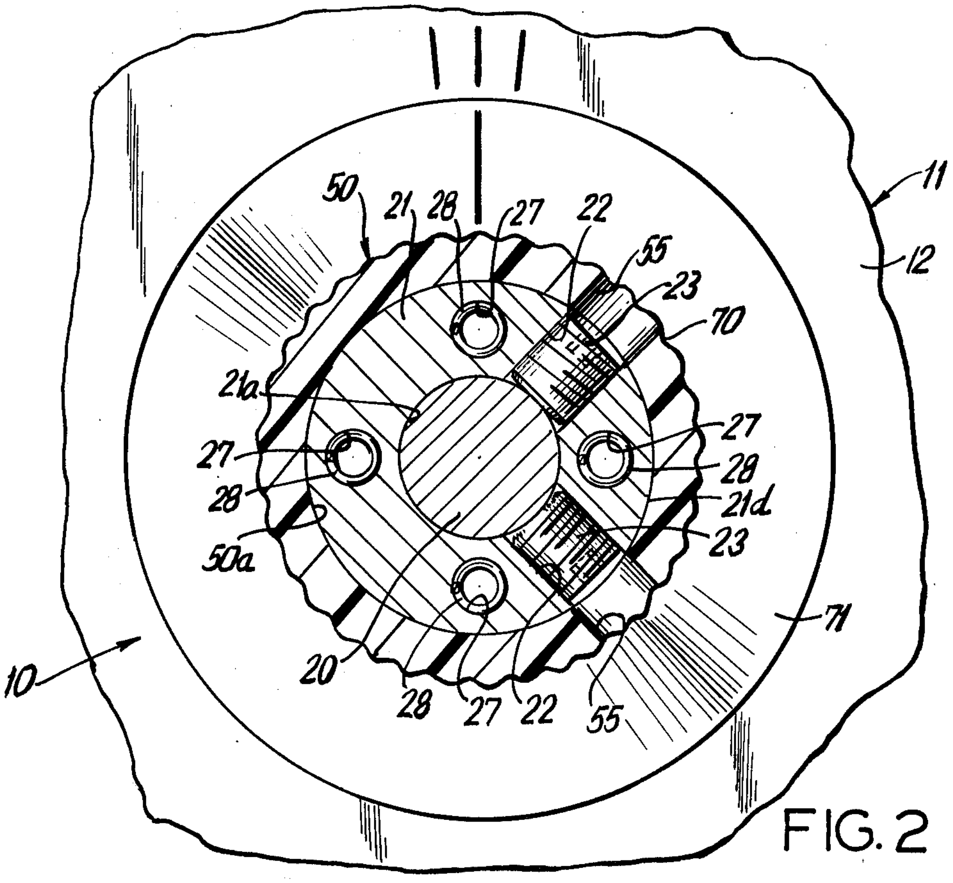
FIG. 2 is a cross-sectional view taken on line 2—2 of FIG. 1.
Figure 3:
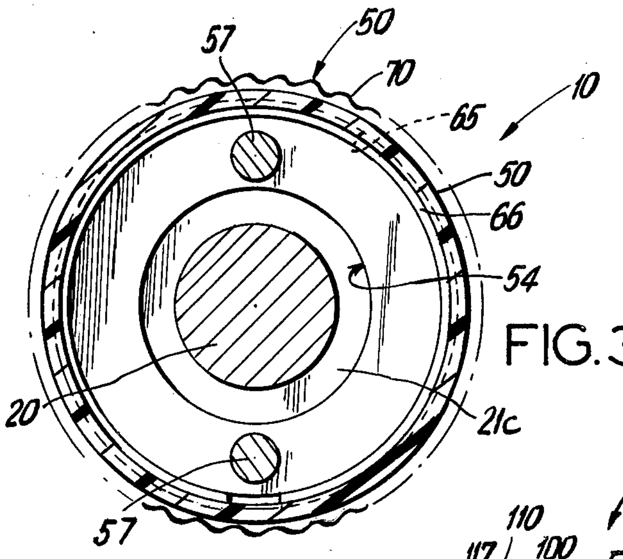
FIG. 3 is a cross-sectional view taken on line 3—3 of FIG. 1.

Referring now in detail to the drawings, particularly to FIGS. 1–3 thereof, 10 designates a knob and control shaft assembly embodying the invention. Said assembly comprises a panel 11 which may be fixed to any suitable apparatus, electrical or mechanical, not shown.

Said panel 11 may comprise a fixed vertical wall 12 provided with a forwardly extending boss 13, and has a horizontal bearing through hole or bore 14. At the front end of the boss 13 are formed a pair of holes 15 parallel to the axis of bore 14, for the purpose hereinafter appearing.

Journalled in bore 14 is a control shaft 20 which extends forwardly beyond the panel 11. Surrounding the forward part of shaft 20 and disposed forwardly of panel 11 is an insert ring 21 formed with a pair of internally threaded radial through openings 22 spaced 90° apart. Screwed into openings 22 are set screws 23 to fix the ring 21 to the shaft. Said set screws 23 when screwed into holes 22, do not extend radially beyond said holes, as shown in FIG. 2.

Said ring 21 has a center through bore **21*a* into which the shaft 20 fits, has a front vertical surface 21*b* and a rear vertical surface 21*c* spaced from the front surface 13*a* of boss 13. Said ring 21 furthermore has an outer front cylindrical surface 21*d* and a rear inwardly tapering frusto-conical surface 25, reducing in diameter rearwardly. Said ring 21 furthermore is formed with four, equiangularly spaced similar bores 27 parallel to the axis of the ring, and extending from the front face 21*b* of the ring but terminating short of the rear face 21*c* of said ring. One of said bores 27 is located angularly equally between the radial holes 22, as shown in FIG. 2. Disposed in each of the bores 27 is a coil compression spring 28 contacting the blind end of the bore but terminating short of the front open end of the bore. Mounted on the insert ring 21 is a knob housing or body 30 having a front end wall 31 having a central inner or rear cavity or hole 32 and an annular vertical rear flat surface 33. Said front wall 31 is formed with four countersunk holes 35 extending forwardly from rear wall 33 and coaxial with the four holes 27 in ring 21, but of larger diameter than the ring holes. The knob body 30 is attached to the ring insert 21 for rotation therewith by means of four pins 40, each having a head 40*a* received in a hole 35 and a stem 40*b* received in a hole 27. The springs 28 are contacted by the stems 40*b* as shown in FIG. 1. The outer surfaces of heads 40*a* are knurled to grip the inside surfaces of the holes 35. The insert ring 21 may have slight longitudinal movement relative to the body 30**, as will appear hereinafter.

Extending rearwardly from the front wall 31 of body 30 is a tubular wall or shirt portion 50 surrounding the ring 21 and overlapping the boss 13 of panel 11. The tubular wall 50 is closed at one end by said end wall 31 and it is open at its other end.

In one position of the knob body, which is the position of FIG. 1, in which position the knob body can turn to rotate the shaft 14, rear surface 33 of front wall 31 contacts front surface 21*b* of the ring. Said skirt 50 has an internal cylindrical surface 50*a* slidably receiving the outer cylindrical surface 21*d* of ring 21. At the rear end of surface 50*a* is an annular rear facing surface 50*b* from which extends an internal cylindrical surface 50*c* of greater diameter than cylindrical surface 50*a*. Surface 50*c* extends to the rear end of skirt 50 and rotatably receives boss 13 at its rear end.

Received in the space 51 between ring 21 and boss 13 is a brake 54 to be described hereinafter.

Said skirt 50 is formed with a pair of through holes 55 registering with internally screw threaded holes 22 and of such diameter as to allow the set screws 23 to pass therethrough with clearance for screwing said set screws into threaded holes 22.

Said brake 54 is in the shape of an annular ring surrounding but spaced from shaft 20. It comprises a rear annular ring portion 54*a* formed with a pair of diametrically spaced holes 54*b* receiving stems 55*a* of pins 56. Pins 56 have heads 57 slidably received in holes 15. This brake 54 cannot rotate but can slide forwardly of the FIG. 1 position thereof.

Extending forwardly from the rear portion 54*a* of brake 54 is a flange 60 surrounding at its forward end, the tapered external surface 25 of insert ring 21, and formed with an internal frusto-conical surface 61 complementary and similar to said tapered external surface.

In the FIG. 1, operative position of the knob, annular shoulder 50*b* of skirt 50 of the knob body 30 contacts the front edge of skirt 60 of the brake and pushes the brake rearwardly to disengage tapered surfaces 25, 61, to allow the knob body to be rotated to rotate the shaft 20.

Means is provided to move the brake 54 forwardly to engage tapered, locking surfaces 25, 61 to prevent rotation of the shaft 20 when the knob body 30 is not pushed in. To this end surface 50*c* of skirt 50 is formed with an internal groove 65 rearwardly of the brake but forwardly of boss 13. Said groove is of semi-circular cross sectional shape. Received in said annular groove 65 is a split ring 66 projecting radially inwardly of internal surface 50*c*. When rearward pressure on the body 30 is relieved in the FIG. 1, position of the device, springs 28 project the body 30 forwardly moving shoulder 50*b* forwardly away from the front edge of skirt 60 and at the same time ring 66 contacts the rear side of the brake 54 and slides it forwardly to cause tapered surface 61 to contact tapered surface 25 to lock the insert ring 21 and the knob body against rotation.

This is a safety feature to prevent rotation of the shaft 20 by vibration or otherwise unless the knob body 30 is first pushed in. The body cannot turn unless it is first pushed in. There must be a positive pushing in action on the knob before the control shaft can be turned.

When inward pushing in on the body is relieved and the body moves forward, shoulder 50 moves forwardly away from the front circular edge of flange 60, thus allowing the brake to be slidably moved forwardly by split ring 66. Springs 28 tend to resiliently press body 30 forwardly to press the tapered surfaces 25, 61 into locking engagement thereby preventing rotation of the body 30, insert ring 21 and control shaft 20.

The outer surface of skirt 50 may be scored or wavy in shape as shown at 70 to aid in turning the body. A dial 71 may be fixedly mounted on the rear end of skirt 50 and marked with indicia cooperating with markings on the front face of panel wall 12 adjacent the dial, to indicate the angular position of the body, and hence the control shaft.

Figure 4:
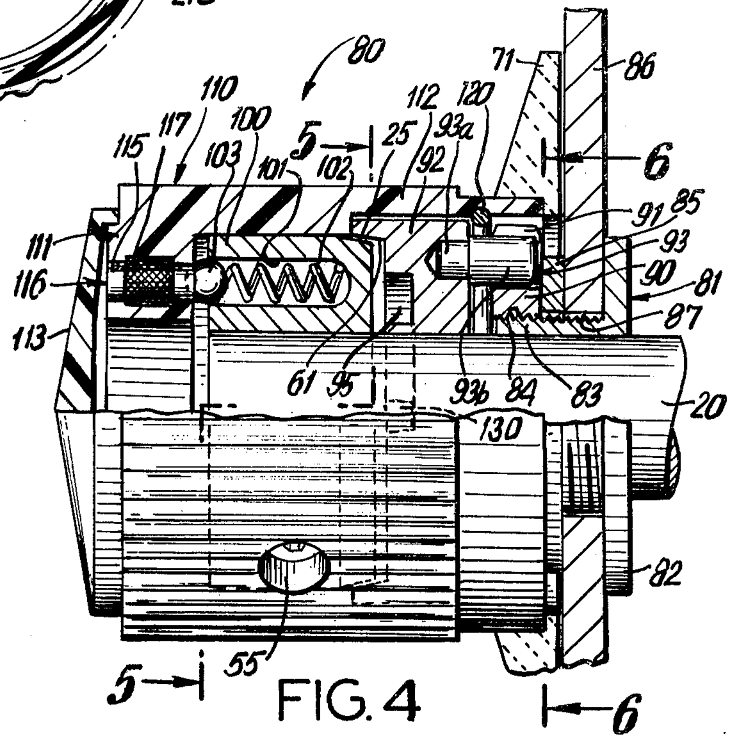
FIG. 4 is a view similar to FIG. 1, but illustrating a modified form of the invention.
Figure 5:
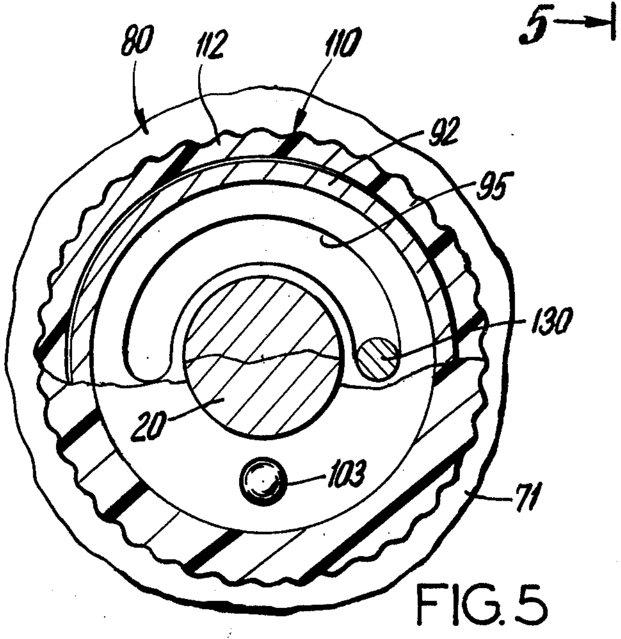
FIG. 5 is a cross-sectional view taken on line 5—5 of FIG. 4.
Figure 6:
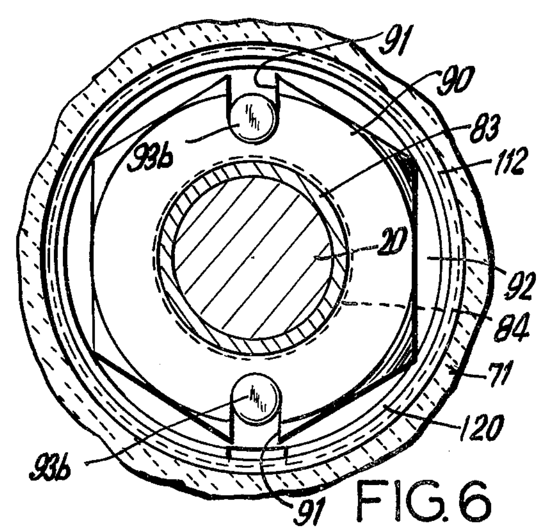
FIG. 6 is a cross-sectional view taken on line 6—6 of FIG. 4.

In FIGS. 4, 5 and 6 there is shown a knob and control shaft assembly 80 illustrating a modified form of the invention. The device 80 comprises a control shaft 20, as in FIGS. 1—3. Surrounding the shaft 20 is a bushing 81 having an annular flange 82 in a vertical plane. Extending from said flange 82 is a sleeve 83 in which the shaft 20 is journalled. Assembled onto the sleeve 83 (which is externally threaded as at 84) is a lock washer 85. The bushing 81 is clamped to panel 86 by flange 82, and lock washer 85 and nut 90 formed with a pair of diametrically opposed outwardly opening notches 91 for purposes hereinafter appearing. Said panel 86 has through opening 87 through which sleeve 83 passes with clearance.

Surrounding the shaft 20 is a brake 92 similar to brake 54 of FIG. 1 except as explained hereinafter. Said brake 92 carries a pair of pins 93 similar to pins 56 and having stems 93*a* received in sockets or holes in the brake member and heads 93*b* similar to heads 57, received in said notches 91 in nut 90.

Said brake 92 is formed at its front side with a part-circular groove 95, shown to be about 180° in angular extent in the drawing, but which could be of any desired angular extent. The purpose of said groove 95 will be explained hereinafter.

Also surrounding the shaft 20 and located forwardly of the brake 92, is an insert ring 100 which may be like ring 21 of FIG. 1, except for differences to be explained hereinafter. Ring 100 has two internally threaded radial holes (not shown), like holes 22 receiving set screws (not shown) like set screws 23 to fix said ring to the shaft.

Said ring has a tapered surface like surface 25 complementary to tapered surface 61 of the brake for locking in the manner similar to the locking of the insert ring and brake of FIG. 1.

Ring 100 is formed with four equiangularly spaced blind bores 101 opening forwardly and housing coil compression springs 102, respectively. The spring 102 of each hole 101 presses against a ball 103 at its forward end for the purpose explained hereinafter. Holes 101 are spaced like holes 27 of FIG. 1.

Device 80 also comprises a body 110 which may be like body 30 except that body 110 has a front annular wall 111 from which a skirt 112 extends rearwardly. Skirt 112 is like skirt 50 of FIG. 1. A front cap 113 is fixed to front wall 111 instead of being integral therewith as in FIG. 1. Annular wall 111 is formed with four through holes 115 aligned with holes 101 and receiving sleeves 116, respectively. On each sleeve 116 is a central enlarged collar 117 knurled externally. The balls 103 are pressed by springs 102 against the rear ends of sleeves 116.

Skirt 112 carries a split ring 120 similar to split ring 66.

The body 110 must be pushed in to move the brake 92 rearwardly away from insert ring 100 before the knob body can be turned for turning the control shaft 20. Turning of the body causes turning of the insert ring 100 because the balls 103 are pressed partially into the openings in the sleeves 116. Turning of the insert ring will turn the shaft 20 by reason of the set screws 23 gripping the shaft 20. However should the torque imposed on the knob body be too great, the body will turn but press the balls rearwardly against springs 102 to allow rotation of the body without rotating the shaft.

Fixed to the rear of the ring 100 is a pin 130 projecting into groove 95, to limit rotation of the knob body to 180° as shown in FIGS. 4–6, or to any other desired angular extent, depending on the angular extent of groove 95.

The angles of the taper of tapered surfaces 25, 61 may be varied as desired to give the desired locking grip when said surfaces contact. The spring 28 or 102 as the case may be resiliently pressing the knob body forwardly when the body is not pushed in, resiliently press the split ring forwardly to cause a resilient pressure of the tapered surface 61 of the brake on the tapered surface 25 of the insert ring to create the locking engagement of said surfaces.

It will be understood that the part circular groove 95 may be employed in the brake 54 of FIG. 1 to receive ring 21, if desired.

The dial 71 of FIG. 1 may be omitted if desired. Such a dial may also be used with the device of FIG. 4.

Also the nut 90 of FIGS. 4 to 6 may be employed with device shown in FIG. 1.

It will thus be seen that there is provided a device in which the several objects of this invention are achieved and which is well adapted to meet the conditions of practical use.

As various possible embodiments might be made of the above invention, and as various changes might be made in the embodiment above set forth, it is to be understood that all matter herein set forth or shown in the accompanying drawings is to be interpreted as illustrative.

Springs 23 can be varied to change the locking forces. The angle of the taper can be varied to change the grip.

With the removal of the four springs 28 associated with the four pins 40 of FIGS. 1–3, the knob body 30 can remain in a locked or an unlocked position. This faciliates continuous rotation of the shaft 20 without necessity for intermittently depressing the knob, to thereby achieve rapid adjustment of the shaft to the desire angular position. Simply pulling the knob will engage the brake mechanism and lock the control shaft until such time as additional changes are required. The knob can then be depressed achieving the initial state above and the process repeated.

The advantages of such construction are fully realized when multi rotational functions are required since the knob can be spun to achieve rapid adjustment.

To review the invention, its features are:

1. To provide a knob which will automatically lock a control shaft in any desired angular positions. This is accomplished when knob is released and internal springs cause tapered clutch faces to engage.
2. To provide said knob with the means to unlock said control shaft and position shaft in any angular position, easily.

This is accomplished when the knob is first pushed in and then rotated by the operator.

3. The accomplishment of the above could not be, without a frame of reference to the control shaft. This is accomplished by means of a serrated nut which is affixed to the threaded bushing, or may be affixed to the control shaft front panel in some other fashion. The serrated nut keys the stationary brake contained within the knob against angular rotation and thus becomes the fixed frame of reference for the knob.
4. To incorporate an overriding clutch as an added feature which prevents the locked control shaft from turning when the knob is rotated with a torque greater than the torque capacity of the clutch faces. This is accomplished by replacing molded-in pin inserts with molded-in recesses and adding the appropriate number of balls, which engage these recesses under spring or other resilient force.

It is to be noted that without this feature the knob can be overtorqued which may result in rotation of the control shaft.

It is still further to be noted that said overriding clutch feature also acts as a slip clutch when the control shaft mechanism contains limit stops.

5. To incorporate limit stops as an added feature which limits the angular rotation of the control shaft, when desired.
6. With the exception to the serrated nut which is a separate item, all components that provide the above functions are contained wholly within the knob body.

In spite of apparent complexity, all knobs are assembled to control shafts in a conventional manner, by means of set screws contained in knob.

We claim:

1. A knob control shaft assembly comprising a control shaft, a ring insert surrounding said shaft, means to fix said ring insert to said shaft, a knob body surrounding said ring insert and slidably mounted thereon, means to connect said knob body to said ring insert for rotatation together therewith, and spring means for sliding said body longitudinal forwardly relative to said ring insert, and ball means interposed between said spring means and knob body, said knob body having means partially receiving the ball means, to allow said knob to rotate relative to said ring insert when a turning torque imposed on said body is sufficient to cause said ball means to compress the spring means, to allow turning of the knob body without turning the ring insert, releasable means to lock the shaft against rotation, and means controlled by sliding movement of the knob relative to the shaft for controlling said lock means.

2. A knob control shaft assembly comprising a control shaft, a ring insert surrounding said shaft, means to fix said ring insert to said shaft, a knob body surrounding said ring insert and slidably mounted thereon, means to connect said knob body to said ring insert for rotation together therewith, and spring means for sliding said body longitudinally fowardly relative to sad ring insert, a brake surrounding said shaft, said knob body surrounding said brake, means to mount said brake against rotation and for longitudinal sliding movement relative to said insert, mutually contacting, releasable interlocking means on said ring insert and brake, means to release said interlocking means upon pushing said knob body rearwardly relative to said shaft, and means on said knob body to move said interlocking means into interlocking relation upon relieving rearward push of said knob body.

3. A knob control shaft assembly comprising a control shaft, a ring insert surrounding said shaft, means to fix said ring insert to said shaft, a knob body surrounding said ring insert and slidably mounted thereon, means to connect said knob body to said ring insert for rotation together therewith, and spring means for sliding said body longitudinally fowardly relative to said ring insert, a brake surrounding said shaft, said knob body surrounding said brake, means to mount said brake against rotation and for longitudinal sliding movement relative to said insert, mutually contacting, releasable interlocking means on said ring insert and brake, and means to release said interlocking means upon pushing said knob body rearwardly relative to said insert, and means on said knob body to move said interlocking means into locking relation upon relieving rearward push of said knob body, and ball means interposed between said spring means and knob body, said knob body having means partially receiving the ball means, to allow said knob body to rotate relative to said ring insert when a turning torque imposed on said body is sufficient to cause the ball means to compress the spring means to allow turning of the knob body without turning the ring insert.

4. The combination of claim 3, and means to limit rotation of said knob body to a predetermined angle of rotation.

5. A knob control shaft assembly comprising a control shaft, a ring insert surrounding said shaft, means to fix said ring insert to said shaft, a knob body surrounding said ring insert and slidably mounted thereon, means to connect said knob body to said ring insert for rotation together therewith, and spring means for sliding said body longitudinally forwardly relative to said ring insert, a brake surrounding said shaft, said knob body surrounding said brake, means to mount said brake against rotation and for longitudinal sliding movement relative to said insert, mutually contacting releasable interlocking means on said ring insert and brake, and means to release said interlocking means upon pushing said knob body rearwardly relative to said insert, and means on said knob body to move said interlocking means into interlocking relation upon relieving rearward push of said knob body, said means to mount said brake against rotation, comprising a panel, a bushing journalling said shaft, means to fix said bushing to said panel, a nut screwed to said bushing and having outwardly opening notches, and pins on said brake received in said notches.

6. A knob control shaft assembly comprising a control shaft, a ring insert surrounding said shaft, means to fix said ring insert to said shaft, a knob body surrounding said ring insert and slidably mounted thereon, means to connect said knob body to said ring insert for rotation together therewith, and spring means for sliding said body longitudinally forwardly relative to said ring insert, a brake surrounding said shaft, said knob body surrounding said brake, means to mount said brake against rotation and for sliding movement relative to said insert, interlocking means on said ring insert and brake, means to release said interlocking means upon pushing said knob body rearwardly relative to said insert, and means on said knob body to move said brake into locking relation to said ring insert upon releasing rearward pushing of knob body, said means to mount said brake against rotation comprising a panel having holes, and pins on said brake received in said holes.

7. A knob control shaft assembly comprising a control shaft a ring insert surrounding said shaft, means to fix said ring insert to said shaft, a knob body surrounding said ring insert and slidably mounted thereon, means to connect said knob body to said ring insert for rotation together therewith, and spring means for sliding said body longitudinally forwardly relative to said ring insert, a brake surrounding said shaft, said knob body surrounding said brake, means to mount said brake against rotation and for sliding movement relative to said shaft, interlocking means on said insert ring and brake, means to release said interlocking means upon pushing said knob body rearwardly relative to said shaft, means on said knob body to move said brake into locking relation to said insert ring upon releasing rearward pushing of knob body, and means to limit rotation of said knob body to a predetermined angle of rotation, said limit means comprising a pin on said insert ring, and said brake having a part circular groove to receive said pin on said insert ring.

8. The combination of claim 7, and ball means interposed between said spring means and knob body, said knob body having means to partially receive the ball means to allow said knob to rotate relative to said insert ring when a turning torque imposed on said body is sufficient to cause the ball means to compress the spring means to allow turning of the knob body without turning the insert ring.

9. A knob and control shaft assembly comprising a control shaft, a panel, a brake surrounding said shaft, means to mount said brake on said panel against rotation relative to said panel, a ring insert surrounding said shaft; means to fix said ring insert to said shaft, a knob body having a front wall, and a skirt surrounding said ring insert and brake, means to connect said knob body to said ring insert for rotation therewith and for sliding movement of said knob body relative to said ring insert, spring means on said ring insert to move said knob body forwardly relative to said ring insert upon releasing rearward pushing of said knob body, said ring insert having a tapered surface, said brake having a complementary tapered surface, means on said knob body to move said brake relative to said ring insert to disengage said tapered surfaces of said ring insert and brake upon pushing said knob body rearwardly relative to said ring insert, to allow rotation of said knob body and ring insert to rotate said control shaft; and means on said knob body to move said brake forwardly to interengage said tapered surfaces for locking said ring insert to said brake, against rotation of said ring insert and knob body and control shaft when said spring means moves said knob body forwardly upon releasing said knob body after it has been pushed rearwardly to disengage said tapered surfaces.

10. The combination of claim 9, said means to fix said ring insert to said shaft comprising radial set screw means screwed into radial threaded opening means in said insert ring, to grip said shaft, said knob having clearance hole means to allow said set screw means to be passed through said clearance hole means for screwing into said internally threaded openings.

11. The combination of claim 10, said brake having a part circular groove in its front face, said insert ring having a pin slidable in said groove.

12. The combination of claim 11, and ball means interposed between said spring means and socket means formed on said knob body, to allow said knob body to be rotated without rotating said insert ring when the torque on said knob body is sufficient to cause said ball means to compress said spring means.

13. The combination of claim 9, and ball means interposed between said spring means and socket means formed on said knob body, to allow said knob body to be rotated without rotating said insert ring when the torque on said knob body is sufficient to cause said ball means to compress said spring means.

14. The combination of claim 9, said brake having a part circular groove in its front face, said insert ring having a pin slidable in said groove.

15. The combination of claim 9, said means to mount said brake on said panel comprising a bushing on said panel, journalling said shaft, a nut on said bushing and having an outwardly opening notch and a pin on said brake received in said notch.

16. A knob control shaft assembly comprising a control shaft, a ring insert surrounding said shaft, means to fix said ring insert to said shaft, a knob body surrounding said ring insert and slidably mounted thereon, means to connect said knob body to said ring insert for rotation together therewith, and for sliding movement of said body longitudinally relative to said ring insert, a brake surrounding said shaft, means for fixing said brake against rotation, said ring insert having a tapered surface, said brake having a complementary tapered surface, means on the knob body to slide said brake relative to said ring insert to disengage said tapered surfaces upon pushing said knob body rearwardly relative to said ring insert, to allow rotation of said knob body together with said ring insert, to thereby rotate said control shaft, and means on said knob body to move said brake forwardly to interengage said tapered surfaces for locking said ring insert to said brake, to prevent rotation of said control shaft.

17. The combination of claim 16, and a dial surrounding said control shaft, and means to so mount said dial that it can rotate with rotation of the shaft.

18. The combination of claim 16, and a dial surrounding said control shaft, and means to so mount said dial that it can rotate with rotation of the shaft.

19. The combination of claim 16, and means to limit rotation of said knob body to a predetermined angle of rotation.

20. The combination of claim 16, a brake surrounding said shaft, said knob body surrounding said brake, means to mount said brake against rotation and for longitudinal sliding movement relative to said shaft, mutually contacting releasable interlocking means on said ring insert and brake, and means to release said interlocking means upon pushing said knob body rearwardly relative to said shaft, and means on said knob body to move said interlocking means into interlocking relation upon relieving rearward push of said knob body, said means to mount said brake against rotation, comprising a panel, a bushing journalling said shaft, means to fix said bushing to said panel, a nut screwed to said bushing and having outwardly opening notches, and pins on said brake received in said notches.

21. The combination of claim 16, a brake surrounding said shaft, said knob body surrounding said shaft, means to mount said brake against rotation and for sliding movement relative to said shaft, interlocking means on said ring insert and brake, means to release said interlocking means upon pushing the knob body rearwardly relative to said shaft, and means on said knob body to move said brake into locking relation to said ring insert.

22. The combination of claim 21, and means to limit rotation of said knob body to a predetermined angle of rotation.

23. A knob assembly for a control shaft comprising a knob housing, said knob housing comprising a tubular wall open at one end and closed at its other end by an end wall, a member housed within said knob housing, cooperative means on said knob housing and member to connect them for relative sliding movement and for rotation together, spring means interposed between said member and said end wall of the knob housing, to cause said knob housing to slidably move forwardly relative to said member, said member having a bore to receive a control shaft, means to fixedly attach said member to a control shaft in said bore, for rotation with said member and against sliding movement relative to such control shaft, means to retain said knob housing in a predetermined normal forwardly moved position when slidably moved fowardly relative to said member by said spring means, brake means housed within the knob housing, to lock said member against rotation when said knob housing is in said normal forward moved position thereof, to prevent rotation of such control shaft when said knob housing is in its normal forwardly moved position, and means to release said brake means upon pushing the knob housing rearwardly relative to said member, to load said spring means and to allow said knob housing to be rotated in said pushed in position of said knob housing to rotate said member therewith and hence to rotate a control shaft fixed to said member, and said loaded spring means moving the knob housing again forwardly to actuate said brake means to locking condition upon removing application of pushing-in pressure on said knob housing and allowing said knob housing to move forwardly, to thereby again lock said member against rotation, to prevent rotation of a control shaft fixedly attached to said member.

24. The combination of claim 23, and said cooperative means of said knob housing and member including means to allow said knob housing to rotate relative to said member when a turning torque imposed on said knob housing exceeds a predetermined degree of torque.

25. The combination of claim 24, said last mentioned means including ball means interposed between said spring means and said end wall of said knob housing.

26. The combination of claim 23, in combination with a control shaft in said bore of said member, a control panel for said control shaft, and means fixed to said control panel to retain said brake against rotation.

27. The combination of claim 23, and means to limit rotation of said knob housing to a predetermined angle of rotation.

28. A knob assembly for a control shaft, comprising a knob, said knob comprising a knob housing having an end wall, and a tubular wall extending therefrom, said tubular wall being open at one end and adapted to receive a control shaft projecting thereinto through said open end, said knob housing being slidable from a normal forwardly extended position to a rearwardly pushed-in position, spring means within said knob housing to slidably move said knob housing from a pushed in position to its normal extended position upon relieving pushing-in pressure on said knob housing, means to connect said knob housing to a control shaft projecting into said knob housing, for sliding movement of said knob housing relative to said shaft and for rotation with said shaft, releasable means disposed within said knob housing, to lock said knob housing against rotation, in said normal extended position thereof, and means to release said lock means, upon pushing said knob housing rearwardly from extended position, to permit rotation of said knob housing together with said shaft.

29. The combination of claim 28, said means to connect said knob to said control shaft for rotation therewith, including means to allow said knob housing to rotate relative to said shaft when a turning torque imposed on said knob housing exceeds a predetermined torque.

30. The combination of claim 29, said last mentioned means including ball means interposed between said spring means and said end wall of said knob housing.

31. The combination of claim 28, in combination with a control shaft projecting into said knob housing through said open end of said knob housing.

32. The combination of claim 31, a control panel for said control shaft, and means on said conrol panel to journal said control shaft.

33. The combination of claim 28, and means to limit rotation of said knob housing to a predetermined angle of rotation.

34. The combination of claim 33, and said lock means comprising means keyed to said control panel against rotation.

35. The combination of claim 28, and said means to connect said knob housing to a control shaft projecting into said knob housing for sliding movement of said knob housing relative to said shaft and for rotation with said shaft, comprising a member housed in said knob housing, and journalling said shaft and means to fix said member to said shaft.

36. The combination of claim 35, said spring means being interposed between said member and said end wall of said knob housing.

* * * * *